(12) United States Patent
Seymour et al.

(10) Patent No.: US 10,493,297 B2
(45) Date of Patent: Dec. 3, 2019

(54) NEUROMODULATION TRANSFECTION SYSTEM WITH PASSIVE FLUID DELIVERY

(75) Inventors: John P. Seymour, Ann Arbor, MI (US); KC Kong, Ann Arbor, MI (US); Rio J. Vetter, Ypsilanti, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 1671 days.

(21) Appl. No.: 13/557,555

(22) Filed: Jul. 25, 2012

(65) Prior Publication Data
US 2013/0030353 A1    Jan. 31, 2013

Related U.S. Application Data

(60) Provisional application No. 61/511,375, filed on Jul. 25, 2011.

(51) Int. Cl.
*A61B 5/04* (2006.01)
*A61N 1/05* (2006.01)
(Continued)

(52) U.S. Cl.
CPC .......... *A61N 5/0622* (2013.01); *C12N 15/87* (2013.01); *A61B 5/04001* (2013.01); *A61N 1/05* (2013.01); *A61N 1/327* (2013.01); *A61N 1/36121* (2013.01); *A61N 2005/063* (2013.01); *A61N 2005/067* (2013.01); *A61N 2005/0612* (2013.01); *A61N 2005/0651* (2013.01); *Y10T 29/49204* (2015.01)

(58) Field of Classification Search
CPC .. A61N 1/0412; A61N 1/0428; A61N 1/0568; A61B 5/04; A61B 5/04001; A61B 5/0476; A61B 5/0478; A61B 5/40; A61B 5/4029; A61B 5/4041; A61B 5/4839; A61B 5/4893; A61B 5/6846; A61B 2017/561; A61B 2018/00154
USPC ........ 600/372–373, 377–378, 393, 544–545; 607/115–118
See application file for complete search history.

(56) References Cited

U.S. PATENT DOCUMENTS 3,628,017 A   12/1971   Lerner
5,629,009 A   5/1997    Laurencin et al.
(Continued)

FOREIGN PATENT DOCUMENTS

WO   2008/089003   7/2008
WO   2009/072123   6/2009
(Continued)

OTHER PUBLICATIONS

Yizhar et al. "Optogenetics in Neural Systems". Neuron Issue 71, Jul. 14, 2011.*
(Continued)

*Primary Examiner* — Joseph A Stoklosa
*Assistant Examiner* — Brian M Antiskay
(74) *Attorney, Agent, or Firm* — Haynes and Boone, LLP; J. Andrew Lowes; Eric Li (57) ABSTRACT

An implantable optical electrode having a thin film electrode array including a plurality of electrodes, a light source associated with the thin film electrode array, and a passive bioactive agent delivery module associated with the thin film electrode array. Also disclosed are methods of manufacturing the array and a neural interface system with passive fluid delivery.

32 Claims, 3 Drawing Sheets

(51) Int. Cl.
*A61N 5/06* (2006.01)
*C12N 15/87* (2006.01)
*A61N 1/32* (2006.01)
*A61N 5/067* (2006.01)
*A61N 1/36* (2006.01)

(56) References Cited

U.S. PATENT DOCUMENTS

| | | | |
|---|---|---|---|
| 6,178,349 B1* | 1/2001 | Kieval | A61N 1/36114 607/118 |
| 6,238,994 B1 | 5/2001 | Derderian et al. | |
| 6,294,074 B1 | 9/2001 | Lin et al. | |
| 7,010,356 B2* | 3/2006 | Jog | A61N 1/0536 600/373 |
| 7,310,546 B2 | 12/2007 | Prass | |
| 7,375,870 B2 | 5/2008 | Schorpp | |
| 7,781,195 B1 | 8/2010 | Heller et al. | |
| 7,955,889 B1 | 6/2011 | Yang et al. | |
| 8,005,526 B2 | 8/2011 | Martin et al. | |
| 8,423,156 B2* | 4/2013 | Boling | A61N 1/0529 607/116 |
| 8,761,889 B2* | 6/2014 | Wingeier | A61N 1/0534 607/116 |
| 2002/0156512 A1* | 10/2002 | Borkan | A61N 1/0551 607/117 |
| 2002/0183682 A1 | 12/2002 | Darvish et al. | |
| 2003/0147958 A1 | 8/2003 | Ahn et al. | |
| 2003/0149462 A1* | 8/2003 | White | A61N 1/046 607/142 |
| 2003/0218130 A1* | 11/2003 | Boschetti | B01J 19/0046 250/288 |
| 2004/0111139 A1 | 6/2004 | McCreery | |
| 2005/0192636 A1* | 9/2005 | Skiba | A61N 1/303 607/2 |
| 2006/0024359 A1 | 2/2006 | Walker et al. | |
| 2006/0287689 A1* | 12/2006 | Debruyne | A61K 9/0046 607/57 |
| 2007/0129780 A1* | 6/2007 | Whitehurst | A61N 1/0556 607/118 |
| 2009/0054954 A1 | 2/2009 | Foley et al. | |
| 2009/0099038 A1 | 4/2009 | Deisseroth et al. | |
| 2009/0118800 A1 | 5/2009 | Deisseroth et al. | |
| 2009/0292325 A1 | 11/2009 | Cederna et al. | |
| 2010/0015095 A1 | 1/2010 | Pan et al. | |
| 2010/0049263 A1 | 2/2010 | Reeve | |
| 2010/0161017 A1 | 6/2010 | Choi et al. | |
| 2010/0190229 A1 | 7/2010 | Zhang et al. | |
| 2010/0191308 A1 | 7/2010 | Meister | |
| 2010/0211172 A1 | 8/2010 | Bellamkonda et al. | |
| 2010/0268150 A1 | 10/2010 | Mohanty et al. | |
| 2011/0021970 A1 | 1/2011 | Vo-Dinh et al. | |
| 2011/0034912 A1* | 2/2011 | de Graff | H01L 27/14687 606/21 |
| 2011/0087126 A1 | 4/2011 | Zorzos et al. | |
| 2011/0093052 A1 | 4/2011 | Anderson et al. | |
| 2011/0105998 A1 | 5/2011 | Zhang et al. | |
| 2011/0112591 A1 | 5/2011 | Seymour et al. | |
| 2011/0144566 A1 | 6/2011 | Dacey, Jr. et al. | |
| 2011/0172736 A1 | 7/2011 | Gefen et al. | |
| 2011/0230747 A1* | 9/2011 | Rogers | A61B 5/05 600/377 |
| 2011/0311489 A1 | 12/2011 | Deisseroth et al. | |
| 2011/0318775 A1 | 12/2011 | Mercola et al. | |
| 2012/0035725 A1 | 2/2012 | Gefen et al. | |
| 2012/0035726 A1 | 2/2012 | Gross et al. | |
| 2012/0130302 A1 | 5/2012 | Wrobel et al. | |
| 2012/0149052 A1 | 6/2012 | Grohovaz et al. | |
| 2013/0030275 A1 | 1/2013 | Seymour et al. | |
| 2013/0030352 A1 | 1/2013 | Seymour et al. | |
| 2013/0144365 A1* | 6/2013 | Kipke | A61B 5/04001 607/93 |
| 2014/0288458 A1* | 9/2014 | Yoon | A61N 1/0529 600/547 |

FOREIGN PATENT DOCUMENTS

| | | |
|---|---|---|
| WO | 2009/124220 | 8/2009 |
| WO | 2009/131837 | 10/2009 |
| WO | 2010/029297 | 3/2010 |
| WO | 2010/056970 | 5/2010 |
| WO | 2010/105728 | 9/2010 |
| WO | 2011/057137 | 5/2011 |
| WO | 2011/057276 | 5/2011 |
| WO | 2012/052727 | 4/2012 |
| WO | 2012/061676 | 5/2012 |
| WO | 2012/061679 | 5/2012 |
| WO | 2012/061688 | 5/2012 |
| WO | 2012/061744 | 5/2012 |
| WO | 2012/075337 | 6/2012 |
| WO | 2013/016389 | 1/2013 |
| WO | 2013/016391 | 1/2013 |

OTHER PUBLICATIONS

Adamantidis et al., "Neural substrates of awakening probed with optogenetic control of hypocretin neurons," Nature, Nov. 2007, vol. 450, pp. 420-425.

Arenkiel et al., "In Vivo Light-Induced Activation of Neural Circuitry in Transgenic Mice Expressing Channelrhodopsin-2," Neuron, Apr. 2007, vol. 54, pp. 205-218.

Dias et al., "New dry electrodes based on iridium oxide (IrO) for non-invasive biopotential recordings and stimulation," Sensors and Actuators A: Physical, 2010, vol. 164, pp. 28-34.

Froehlich et al., "Messung Und Analyse Monophasischer Aktionspotentiale Mit Hilfe Fraktal Beschichteter Elektroden—Teil I," Biomedizinsche Technik, Fachverlad Schiele Und Schoen GmbH, Berlin, DE, vol. 40, No. 6, Jun. 1, 1995, pp. 154-159.

Gradinaru et al., "Targeting and Readout Strategies for Fast Optical Neural Control In Vitro and In Vivo," The Journal of Neuroscience, Dec. 2007, vol. 27(52), pp. 14231-14238.

Light-Induced Artifact, Retrieved from the Internet on Jun. 21, 2012 <URL: http://www.openoptogenetics.org/index.php?title=Light-Induced_Artifact>.

Lu Y et al: "Electrodeposited polypyrrolejcarbon nanotubes composite films electrodes for neural interfaces", Biomaterials, Elsevier Science Publishers BV., Barking, GB, vol. 31, No. 19, Jul. 1, 2010, pp. 5169-5181.

Pachnis, Neutralisation of myoelectric interference from recorded nerve signals using models of the electrode impedance, University College London Department of Electronic and Electrical Engineering, Sep. 2010.

PCT/US2012/048073 International Search Report and Written Opinion dated Oct. 17, 2012 (11 pages).

PCT/US2012/048075 International Search Report and Written Opinion dated Nov. 21, 2012 (17 pages).

PCT/US2012/048076 International Search Report and Written Opinion dated Oct. 17, 2012 (8 pages).

Shimada, "Neural Function Observation with Microelectrode Array," NIT Technical Review, Aug. 2009, vol. 7, No. 8, pp. 1-5.

Zhang et al., "Channelrhodopsin-2 and optical control of excitable cells," Nature Methods, Oct. 2006, vol. 3, No. 10, pp. 785-792.

Zhang et al., "Circuit-breakers: optical technologies for probing neural signals and systems," Neuroscience, Aug. 20007, vol. 8, pp. 577-581.

Zhang et al., "Multimodal fast optical interrogation of neural circuitry," Nature, Apr. 2007, vol. 446, pp. 633-641.

Aravanis et al., "An optical neural interface: in vivo control of rodent motor cortex with integrated fiberoptic and optogenetic technology," Journal of Neural Engineering, 2007, vol. 4, pp. S143-S156.

Bernstein et al., "Prosthetic systems for therapeutic optical activation and silencing of genetically-targeted neurons," Proc Soc Photo Opt Instrum Eng, 2008, 6854, 68540H.

Farah et al., "Patterned Optical Activation of Retinal Ganglion Cells," Proceedings of the 29th Annual International Conference of the IEEE EMBS, Cité Internationale, Lyon, France, Aug. 23-26, 2007, pp. 6368-6370.

(56) References Cited

OTHER PUBLICATIONS

Royer et al., "Light activation and detection of hippocampal neurons in the behaving rat," Presentation Abstract, Neuroscience, Nov. 17, 2008.
Villalobos et al., "All-optical control of neuronal function via optical delivery of light-sensitive proteins and optogenetic stimulation," 2012 BiOs, SPRI Photonics West, 8207G-178, Session 7, p. 65.
Zhang et al., "Integrated device for optical stimulation and spatiotemporal electrical recording of neural activity in light-sensitized brain tissue," J Neural Eng, Oct. 2009, vol. 6(5), pp. 1-24.
Zhang et al., "A Microelectrode Array Incorporating an Optical Waveguide Device for Stimulation and Spatiotemporal Electrical Recording of Neural Activity," 31st Annual International Conference of the IEEE EMBS, Minneapolis, Minnesota, USA, Sep. 2-6, 2009, pp. 2046-2049.

* cited by examiner

NEUROMODULATION TRANSFECTION SYSTEM WITH PASSIVE FLUID DELIVERY

CROSS-REFERENCE TO RELATED APPLICATIONS

This application claims the benefit of U.S. Provisional Application No. 61/511,375, filed Jul. 25, 2011, which is incorporated herein by reference in its entirety.

BACKGROUND

The present invention relates to neural devices, and in particular to a new and useful neuromodulation transfection system.

Various research and clinical neuroscience applications may involve a combination of different techniques for perturbing neural circuits and measuring a response of the perturbed circuit, where the responses of the cells are typically sensed and/or recorded with neurosensing electrodes. Stimulation may be electrical such as with conductive electrode sites, or may be optical such as with optogenetic tools. Optogenetics is a developing technique that uses light-sensitive ion channels for optical stimulation of neural tissue, which allows experimenters or medical practitioners to selectively excite and/or silence particular neural pathways with high precision. To create such light-sensitive ion channels, a viral vector carrying an opsin such as ChR2 or Halorhodopsin (either in the form of DNA code or as a protein) is introduced, for example using surgical methods, into target tissue with cell-type specificity. Electroporation (also known as electropermeabilization), in which an externally applied electric field increases the permeability of a cell membrane, may also be performed as part of the surgery to facilitate delivery of the viral vector. To subsequently utilize the optical neural manipulation techniques, yet another surgical technique is required to introduce an optical stimulator, electrical stimulator, and/or neurosensing components. In other words, the combined use of these neuroscience techniques requires multiple separate surgeries and/or implants. However, each additional procedure or implant increases the difficulty of spatially co-locating the biologics (e.g. relating to electroporation and viral vector delivery), optical light source, neurosensing components, and other components such as drug delivery devices for therapeutic agents. Furthermore, performing multiple surgical procedures may risk creating complications for the subject or patient.

Thus, there is a need in the neural device field for a new and useful neuromodulation transfection system.

SUMMARY

In one embodiment, the invention provides an implantable optical electrode having a thin film electrode array including a plurality of electrodes, a light source associated with the thin film electrode array, and a passive bioactive agent delivery module associated with the thin film electrode array.

In another embodiment, the invention provides a method of manufacturing an implantable optical electrode. The method includes steps of producing a thin film electrode array including a plurality of electrodes and a light source associated with the thin film electrode array; and coupling a passive bioactive agent delivery module with the thin film electrode array.

In yet another embodiment, the invention provides a neural interface system with passive fluid delivery. The system includes an implantable optical electrode having a thin film electrode array comprising a plurality of electrodes, a light source associated with the thin film electrode array, and a passive bioactive agent delivery module associated with the thin film electrode array. The system also includes an electrical subsystem in communication with the electrode array and an optical subsystem in communication with the light source.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
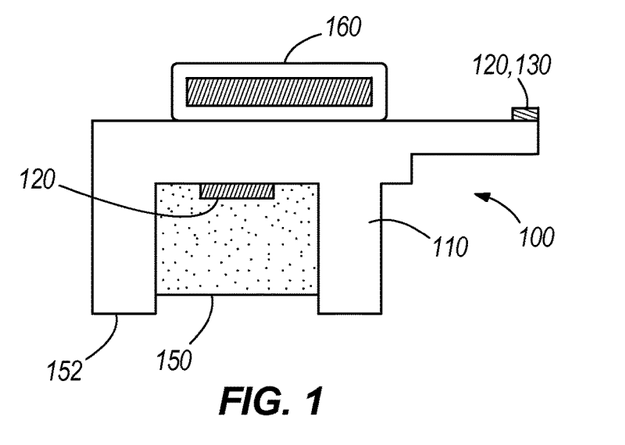
FIG. 1 is a cross-sectional view (as viewed from the bottom of FIG. 2) of one embodiment of a neuromodulation transfection system.
Figure 2:
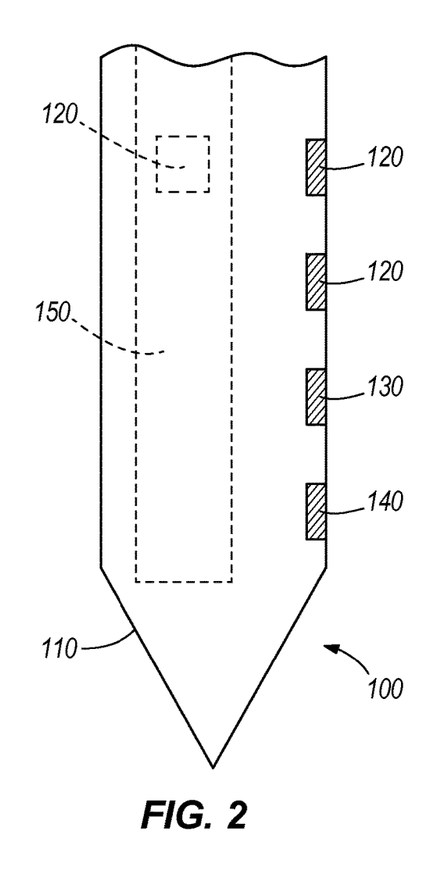
FIG. 2 is a side view of the a neuromodulation transfection system of FIG. 1 with the light source omitted for clarity.
Figure 3:
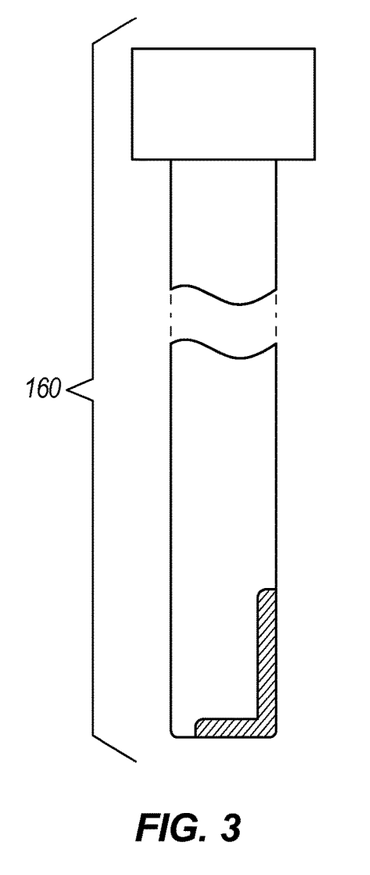
FIG. 3 is a schematic of an embodiment of a waveguide for use with a neuromodulation transfection system.

As shown in FIGS. 1-3, a neuromodulation transfection system 100 according to one embodiment includes a neural interface array 110 insertable in tissue (also referred to herein as an implantable optical electrode) and having an electrode array including one or more electrodes. In some embodiments the electrode array includes at least one neurosensing electrode 120. As shown in FIGS. 1 and 2, the neural interface array 110 includes a delivery capsule 150 coupled to the neural interface array 110 and configured to passively release a bioactive agent to the tissue into which the neural interface array 110 is implanted. The neural interface array 110 includes a light source 160 such as a waveguide or LED coupled thereto, the light source 160 configured to optically stimulate selectively-targeted tissue. In some embodiments, the system 100 further includes neurostimulation electrodes 130 to provide electrical stimulation to the target tissue, for example to stimulate neural activity, and/or electroporation electrodes 140 to permeabilize cells.

The neuromodulation transfection system 100 is multifunctional in that it can, in various embodiments, deliver biologic agents such as light-sensitive opsins (e.g. ChR2 or Halorhodopsin) and/or therapeutic bioactive agents to a targeted tissue region, selectively create electric fields to achieve effective electroporation in the targeted tissue region, selectively optically stimulate particular regions in the targeted tissue region, and sense neural activity in the targeted tissue region. The neuromodulation transfection system 100 in some embodiments is implanted in a particular tissue location in a single surgical procedure, which enables accurate spatial co-localization of the biologic and bioactive agents, electroporation, optical and electrical neurostimulation, and neurosensing, and reduces the number of separate surgeries and implants that may be endured by the subject. In one embodiment, the neuromodulation transfection system 100 may be implanted in brain tissue, but in other embodiments may be implanted in or around other neural tissue (e.g. spinal cord or peripheral nerves) or other suitable tissue (e.g. muscle or heart). Implantation of the neuromodulation transfection system 100 may in various embodiments be partial or complete. In some embodiments, implantation may be performed in a manner that provides access for electrical and optical communications as needed. In some embodiments the neuromodulation transfection system can be a completely implanted and self contained unit.

The neural interface array 110 functions to provide a medium for interaction with surrounding tissue. The neural interface array 110 includes a plurality of electrodes, which can include one or more neurosensing (or recording) electrodes 120. The neural interface array 110 may also include one or more neurostimulation electrodes 130 that electrically stimulate selected tissue regions, such as to elicit neural signals, and/or one or more electroporation electrodes 140 that emit an electrical field to stimulate electroporation of targeted cells. Within each electrode array, the electrodes may be individually and independently controllable, but at least a portion may alternatively be functionally grouped together, so as to form a selectively controllable composite macroelectrode from a group of individual microelectrodes. Additionally, each of electrodes may be used for multiple purposes, including neurosensing, neurostimulation, and electroporation. Sensing and stimulating electrodes may in some embodiments have similar properties, but in other embodiments properties may differ depending on design requirements. Sensing electrodes with a small geometric area are generally suitable for small spatial volume sensing, whereas sensing electrodes having a larger geometric area are suitable for large volume (beyond the single cellular domain) sensing and lower power consumption during stimulation. The electroporation electrodes 140 may be selectively operated in a pattern to create an electrical field that induces molecular movement and/or electropermeabilization along a desired pathway in a targeted region of tissue. In particular, the electroporation electrodes 140 may be coupled to an external voltage driver that controls the electric field emitted by the electroporation electrodes 140.

In some embodiments, the neural interface array 110 may have a circular, cylindrical, or elliptical shank, such as a rolled array or an array wrapped around a carrier. In such embodiments, some or all of the electrodes may be ring electrodes, or circular or elliptical electrodes distributed longitudinally along and/or circumferentially around the carrier. In another embodiment, the neural interface array 110 may be planar (e.g. coupled to a planar carrier or formed as a sheet or rectangular shank) and the electrodes may be distributed along a face and/or edge of the neural interface array 110, depending on the particular application of the system. For example, some or all of the electrodes may be arranged on a lateral edge projection of the neural interface array 110. However, the electrodes may be distributed on the neural interface array 110 in other suitable arrangements. In various embodiments, the carrier or neural interface array 110 may include a sharpened distal point to aid insertion of the system 100 into tissue (e.g. as shown in FIG. 2). In yet another embodiment, the electrodes may instead be integrated with a neural interface array 110 that is configured to wrap around tissue such as the spinal cord.

Figure 6:
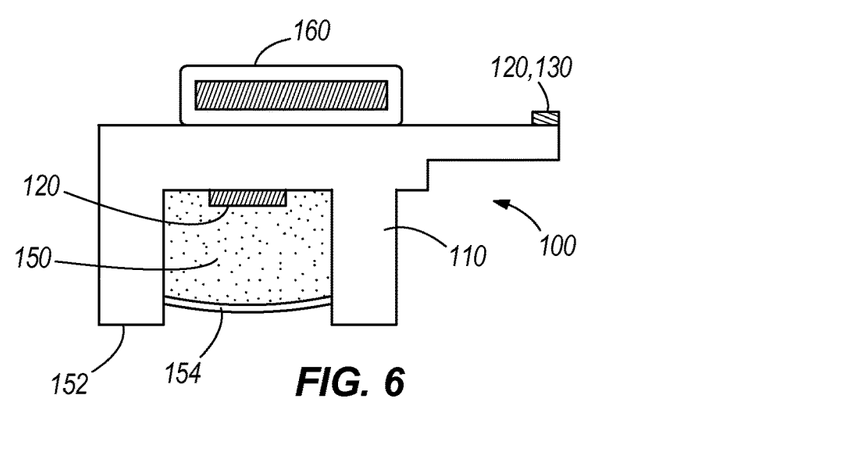
FIG. 6 is a cross-sectional view of another embodiment of neuromodulation transfection system.

As shown in FIG. 1, the neural interface array 110 in. some embodiments further includes a cavity 152 that receives the delivery capsule 150. The delivery capsule 150 along with the mechanisms for coupling the delivery capsule 150 to the neural interface array 110 (for example the cavity 152) are collectively referred to herein as a passive bioactive agent delivery module. The cavity 152 in some embodiments may be made of "walls" that project from the neural interface array 110 and at least partially surround the delivery capsule 150 (FIG. 1). In other embodiments, the cavity 152 may be a recess in the neural interface array 110. The cavity 152 may be located adjacent to or otherwise nearby the neurosensing electrodes 120 or other electrodes, such that the neurosensing electrodes 120 are able to sense at least some of the same region of tissue that is affected by the bioactive agent. Similarly, in some embodiments one or more neurostimulation electrodes 130 and/or electroporation electrodes 140 may be adjacent to the cavity 152 and the delivery capsule 150 in order to stimulate and/or electroporate at least some of the same region. of tissue that is affected by the bioactive agent. The cavity 152 in some embodiments has an open side to improve accessibility of the biologic and bioactive agents to adjacent tissue. For instance, the cavity 152 may be a channel or trench defined longitudinally along a front or back face of the neural interface array 110. Alternatively, the cavity 152 may have slots or other apertures and/or a permeable membrane 154 that exposes surrounding tissue, in one or more directions, to the contents of the cavity 152 (FIG. 6). In another alternative embodiment, the neural interface array 110 itself may be impregnated with a bioactive agent which is then released into the tissue. In embodiments such as this, the neural interface array 110 may be made from materials such as SU-8, KMPR, polyimide, or silicone. In general, these embodiments are carried out using materials that can be processed in relatively thick layers (e.g. >10 μm) so that the reservoir is of suitable volume. In some embodiments the cavity 152 may include multiple delivery capsules that can release the same or different agents, for example at different times. In other embodiments, the neural interface array 110 may include more than. one cavity 152, for example with each cavity 152 having a different delivery capsule.

As noted above, the cavity 152 of the microfabricated neural interface array 110 may in some embodiments be in the form of a recess on one side where the passive delivery capsule 150 may be placed for mechanical support during implantation into neural tissue or placement onto neural tissue. The bioactive agents in the capsule may be made using methods such as those described below, with the additional advantages in this instance that the recess of the neural interface array 110 may provide either mechanical support and/or further control of the release rate, such as by controlling the surface to volume ratio (e.g., the covered side walls). The capsule 150 may be fabricated (e.g. through microembossing) such that it is smaller than the cavity 152 of the neural interface array 110 to enable easy placement and can later be matched to the dimensions of the cavity 152 through methods such as heating and solvent application.

The capsule 150 may also be directly printed into this region using 3-D micro-print technology, or other suitable methods.

In various embodiments, the delivery capsule 150 may be made from a variety of materials including gelatin (or gelatin-like products such as MATRIGEL®), hydrogels, poly-epsilon-caprolactone, polylactic acid, polyglycolic acid, or poly(lactic-co-glycolic acid) (PGLA), or other suitable biodegradable polymer materials. The delivery capsule 150 may be formed as a separate component which is then attached to the neural interface array 110 (e.g. inserted into the cavity 152) or the delivery capsule 150 may be formed on the neural interface array 110. In some embodiments, the delivery capsule 150 may be made using methods such as those described in U.S. Pat. No. 5,629,009 and US 2003/0147958, each of which is incorporated herein by reference in its entirety. In general the delivery capsule 150 includes a matrix in which biologic and/or bioactive agents may be trapped, typically in an aqueous environment, and from which the biologic and/or bioactive agents may be released, for example by diffusing out of the matrix and/or by degradation of the matrix leading to release of the biologic and/or bioactive agents.

In some embodiments an electrode may be located inside of the cavity 152 in which the delivery capsule 150 is located. FIG. 1 shows one possible embodiment in which a neurosensing electrode 120 is located inside the cavity 152 and, upon assembly, the neurosensing electrode 120 is covered by the delivery capsule 150, although in various other embodiments one or more neurostimulation electrode 130 and/or electroporation electrode 140 may be located inside the cavity 152. In the embodiment shown in FIG. 1, the neurosensing electrode 120 inside the cavity 152 can be used to monitor (e.g. using impedance measurements) the rate of degradation of the delivery capsule and/or release of biologic and/or bioactive agents from the delivery capsule 150, in addition to monitoring electrical signals from the tissue.

The rate of release of biologic and/or bioactive agents from the delivery capsule 150 may be controlled by factors such as the density of the matrix in the delivery capsule 150, the rate of degradation of the delivery capsule 150, and/or a rate of diffusion of the biologic and/or bioactive agents through a membrane 154 (see below) which covers the delivery capsule 150. In some embodiments the delivery capsule 150 may be a solution of biologic and/or bioactive agents disposed in the cavity 152 with a membrane 154 covering the cavity 152 to regulate release.

Figure 4:
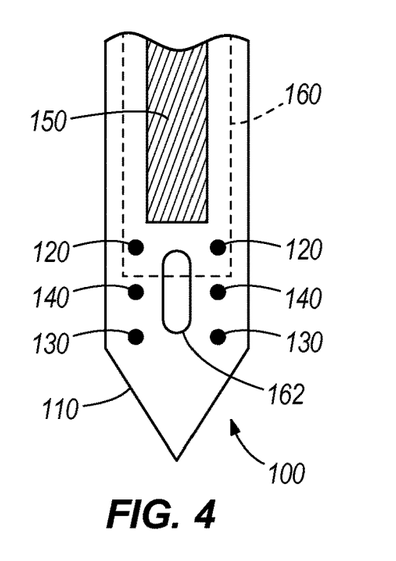
FIG. 4 is a front view of an embodiment of a neuromodulation transfection system.
Figure 5:
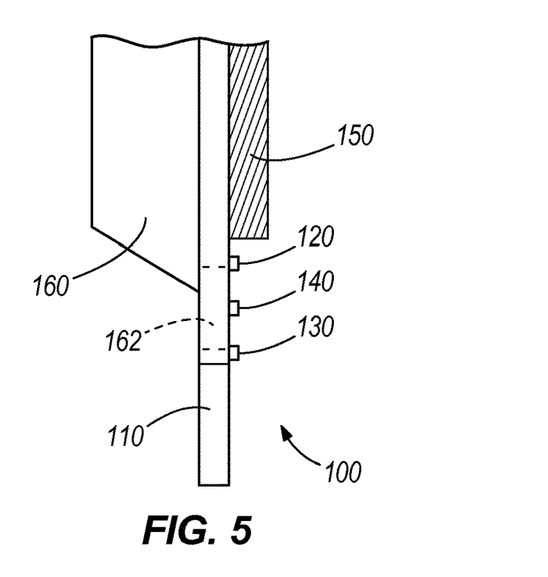
FIG. 5 is a side view of the neuromodulation transfection system of FIG. 4.

As shown in FIGS. 4 and 5, the neural interface array 110 may further include one or more optical port 162, such as an aperture or a window with an optically diffusive material, that allows passage of optical light from the light source 160, such as the waveguide shown in FIG. 5. The optical port 162 may be accompanied with light directing elements that direct light from the waveguide, such as the ports and light directing elements described in US 2011/00112591 (hereinafter referred to as the '591 publication), which is incorporated in its entirety by this reference.

The neural interface array 110 in some embodiments is flexible but may alternatively be rigid or semi-rigid. The neural interface array 110 in various embodiments is a thin-film array fabricated on a wafer, a glass substrate as large as the device, or on a large rolled polymer. Common thin-film techniques, such as used in semiconductor, microelectromechanical system (MEMS), flat panel technology, or roll-to-roll manufacturing may be used to create the neural interface array 110 with standard deposition, photolithography, laser ablation, and etching techniques. Common substrate materials include SU-8, polyimide, parylene, silicone, etc. and/or other suitable materials. In particular, the neural interface array 110 may be formed by micromachining and/or other microfabrication techniques, such as semiconductor manufacturing processes that are known and readily understood by one ordinarily skilled in the art. For instance, the neural interface array 110 may include a plurality of conductive layers deposited on a substrate and patterned to form the neurosensing electrodes 120, neurostimulation electrodes 130, and/or electroporation electrodes 140, such as gold, platinum, iridium, titanium nitride, PEDOT, or other suitable conductive materials. The conductive layers may be additionally protected from the in vivo environment by the deposition and patterning of thin layer(s) of dielectric materials such as silicon carbide, silicon dioxide, and/or diamond at appropriate temperatures. Furthermore, the optical ports 162 may be formed through patterned etching or other suitable microfabrication processes. The neural interface array 110 in various embodiments may further include insulating layers and conductive traces or interconnects that couple to the electrode sites and transmit signals to and from external instrumentation and the electrodes. However, the specific structure and formation of the electrode sites may depend on the particular application of the system. However, the specific structure and formation of the electrode sites may depend on the particular application to which the neuromodulation transfection system 100 is applied. By having components made using thin-film or MEMS methods, one can readily combine the optical, fluidic, and electrical components of the neuromodulation transfection system for various applications and various subject anatomy by changing as few as one photolithographic step in the entire manufacturing process.

The delivery capsule 150 functions to passively release a biologic or bioactive agent to the tissue. The biologic or bioactive agent may be light-sensitive opsins (e.g. ChR2 or Halorhodopsin), drugs or other therapeutic bioactive agents, and/or other suitable fluids or other substances. Light-sensitive opsins such as ChR2 or Halorhodopsin may be delivered in the form of a nucleotide (e.g. as part of a vector such as a viral vector) or in the form of a protein (e.g. as part of a liposome). In some embodiments, cooperation between the delivery capsule 150 and the electroporation electrodes 140 may enable transfection, which introduces nucleic acids into selected cells to facilitate transformation of the cells to subsequently perform optogenetic techniques. The delivery capsule 150 in some embodiments may be coupled to the neural interface array 110 inside a cavity 152, as discussed above, but may alternatively be coupled to a wall, edge, or other suitable surface of the neural interface array 110. Also as noted above, the system 100 in some embodiments may include multiple delivery capsules 150 for different contents. The coupling of the delivery capsule to the neural interface array 110 can also be used to modify the degradation rate and/or the release rate of the delivery capsule 150 by controlling the amount of surface area of the delivery capsule 150 that is exposed to tissue. Embodiments of the neural interface array 110 and delivery capsule 150 such as that shown in FIG. 1 include a single exposed delivery capsule 150 surface, however in other embodiments this may be modified by the structure and porosity of the neural interface array 110 in order to expose more surfaces of the delivery capsule 150.

In one embodiment, as shown in FIG. 1, the delivery capsule 150 is a matrix in which the biologic or bioactive agent is embedded, in which the matrix gradually is resorbed or otherwise degrades to passively release the agent into the surrounding tissue. In another embodiment, as shown in FIG. 6, the delivery capsule 150 is sealed by a membrane 154. For example, the delivery capsule 150 may be an enclosed membrane sac, or formed by sealing the cavity 152 of the neural interface array 110 with a membrane 154. The membrane 154 may be porous such that the capsule 150 contents may be released through the membrane 154, or the membrane 154 may be resorbable or otherwise degradable to release the contents. As noted above for the matrix, degradation of the membrane 154 may be accelerated by adding a suitable fluid or other substance. In yet another embodiment, the delivery capsule 150 may release its contents to surrounding tissue in response to selective exposure to an electrical field, such as described in US 2006/0024359, which is incorporated herein by reference in its entirety. In additional embodiments, the delivery capsule 150 may release its contents to surrounding tissue in response to selective exposure to a particular parameter such as pressure, temperature, or pH. However, the system 100 may alternatively include other suitable kinds of delivery capsule 150. Furthermore, in another alternative embodiment the system 100 may include a coating on the neural interface array 110 and/or waveguide, where the coating includes the biologic or bioactive agent.

The light source 160 (e.g. a waveguide or LED) of the neuromodulation transfection system 100 functions to optically stimulate selected tissue. In some embodiments, the light source 160 includes a waveguide that is coupled to an optical light source such as a light-emitting diode (LED), a laser diode, or other suitable laser or light source, such that the waveguide carries and/or redirects light from the optical light source. The optical light source to which the waveguide is coupled may be located on the neural interface array 110 or at a location remote from the neural interface array 110 including, for example, outside the body. The light source 160 may have selectively-adjustable parameters, such as duration, intensity, and wavelength.

In certain embodiments the neuromodulation transfection system 100 may include an electrical subsystem that functions to operate with the neural interface array 110. The electrical subsystem includes at least one of several variations of suitable electronic subsystems to operate with the neural interface array 110 or combinations thereof. The electrical subsystem may be a printed circuit board with or without onboard integrated circuits and/or on-chip circuitry for signal conditioning and/or stimulus generation, an Application Specific Integrated Circuit (ASIC), a multiplexer chip, a buffer amplifier, an electronics interface, an implantable pulse generator (which produces signals such as a high-frequency, pulsed electric current), an implantable rechargeable battery, integrated electronics for either real-time signal processing of the input (recorded) or output (stimulation) signals, other suitable electrical subsystem, or combinations thereof, as shown in US 2011/0093052 (hereinafter referred to as the '052 publication), which is incorporated in its entirety by this reference.

In those embodiments which employ a waveguide as part of the light source 160, the waveguide may further function as a carrier or other structure for providing support for the system 100. Further, the waveguide may be constructed as part of a thin-film structure made of a light-propagating material such as silicon oxynitride ($SiO_xN_y$), $SiO_2$, silica, $S_3N_4$, SU-8, Cytop, or other suitable material, formed by one or more of several suitable fabrication processes including: micro-opto-electro-mechanical systems (MOEMS), photolithography, microembossing, thermal nanoimprint lithography (NIL), combined nanoimprinting and photolithography (CNP), and/or other suitable fabrication processes. Alternatively, the waveguide may include an optical fiber or other suitable structure. The waveguide may include a refractor, reflector, lens, scattering element, or other light directing elements that direct light from the optical light source. In other embodiments the waveguide may be similar to those described in the '591 publication, and in still other embodiments the waveguide may be other suitable kinds of optical light propagator. In certain embodiments, the waveguide may include an inner core with a cladding layer over the core, such that the core and cladding material facilitate internal reflection along the waveguide. Furthermore, as shown in FIG. 3, the cladding layer may be etched to include one or more apertures or diffusion ports through which the carried light from the optical light source may pass. The diffusion ports of the waveguide may diffuse directly to targeted tissue and/or be aligned with optical ports of the neural interface device.

In various embodiments, at least some of the neurostimulation electrodes 120, neurosensing electrodes 130, and/or electroporation electrodes 140 may be proximate to the delivery capsule 150, such that some electrodes are approximately co-localized with the portion of tissue that includes cells that receive the contents of the delivery capsule 150. In particular, the neurosensing electrodes 120, neurostimulation electrodes 130, electroporation electrodes 140, and locations of emission of bioactive agents and/or optical stimulation are in some embodiments adjacent to one another such that the same tissue regions (targeted cells) may be electropermeabilized by the electroporation electrodes 140, receive bioactive agents, be optically stimulated by the light source 160 (e.g. through the optical ports 162), electrically stimulated by neurostimulation electrodes 130, and/or sensed by neurosensing electrodes 120 without repositioning the implanted system 100 or replacing the implanted system 100 with another device.

Figure 7:
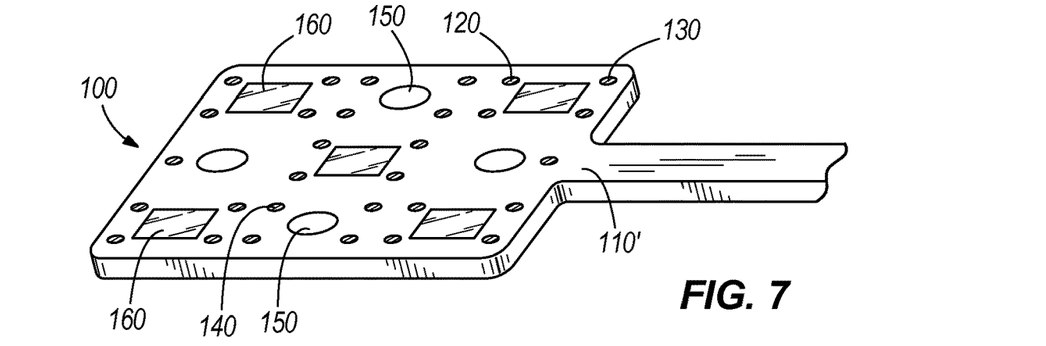
FIG. 7 is a perspective view of an embodiment of a neuromodulation transfection system.

For example, in another embodiment as shown in FIG. 7, the system 100 may include a substantially planar neural interface array 110', such as for covering a tissue surface (e.g., brain or muscle). The planar neural interface array 110' may additionally and/or alternatively be configured to wrap around tissue such as the spinal cord. The planar neural interface array 110' may include a channel or cavity 152 which may be coupled to the surface of the planar neural interface array 110' and/or be embedded within the substrate of the planar neural interface array 110'. The planar neural interface array 110' may include distributed neurosensing electrodes 120, neurostimulation electrodes 130, and/or electroporation electrodes 140, and one or more light sources 160 (e.g., LEDs or waveguides). The planar neural interface array 110' may include one or more portions having a bioactive coating or delivery capsule 150 that allow for passive release of biologic or bioactive agents from the system 100. In various embodiments, each type of electrode, optical light emission, and bioactive agent emission may be interspersed and distributed in an approximately regular pattern. In particular embodiments, each of the array of electrodes, cavity, and light source may be modular and arrangeable in custom relative positions to suit particular applications.

Figure 8:
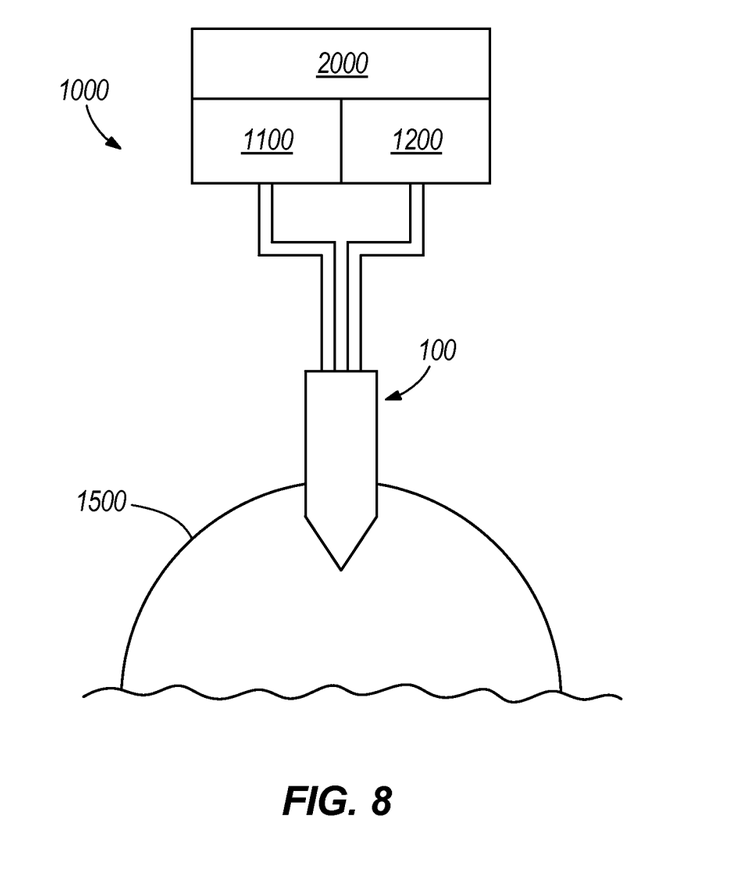
FIG. 8 shows an embodiment of a system for use with embodiments of the disclosed neuromodulation transfection system.

In certain embodiments the neuromodulation transfection system 100 is part of a neural interface system 1000, which may include an electrical subsystem 1100, an optical subsystem 1200, and a controller 2000. The electrical subsystem 1100 functions to operate with the neural interface array 110, for example when the neuromodulation transfection system 100 is implanted into a subject 1500 (FIG. 8). The subject 1500 may include any number of animals into which the neuromodulation transfection system 100 may be implanted and with which the neural interface system 1000 may be employed, including without limitation rodents (e.g. rats, mice, rabbits, etc.) and primates (e.g. humans, monkeys, etc.).

The controller 2000 may control the electrical subsystem 1100 and/or the optical subsystem 1200 to carry out the functions of the neural interface system 1000 such as those disclosed herein. The electrical subsystem 1100, optical subsystem 1200, and controller 2000 may be integrated into a single unit or may be separate units, and each may be external to the subject 1500 or may be part of an implanted device. Each of the electrical subsystem 1100, optical subsystem 1200, and controller 2000 may include a processor, memory, storage, input/output mechanisms, and communication mechanisms, including capabilities for wired and/or wireless communications within the components of the system 1000 and between the system 1000 and external computers and networks.

The electrical subsystem 1100 includes at least one of several variations of suitable electronic subsystems to operate with the neural interface array 110 or combinations thereof. The electrical subsystem 1100 may be a printed circuit board with or without onboard integrated circuits and/or on-chip circuitry for signal conditioning and/or stimulus generation, an Application Specific Integrated Circuit (ASIC), a multiplexer chip, a buffer amplifier, an electronics interface, a pulse generator (which produces signals such as a high-frequency, pulsed electric current, and which in certain embodiments may be implantable), a power supply (which in various embodiments can include an implantable rechargeable battery), integrated electronics for signal processing of the input (recorded) or output (stimulation) signals (either of which may be processed in real time), other suitable electrical subsystem, or combinations thereof, as disclosed in the '052 publication.

The optical subsystem 1200 includes power and control units to control the light source 160 in order to generate light pulses of suitable wavelength, duration, intensity, and pulse shape. The light source 160 (either directly or via a waveguide) functions to illuminate surrounding tissue and stimulating targeted tissue in a manner where the light is parallel, perpendicular, or at other angles relative to the electrodes.

Thus, the invention provides, among other things, an implantable optical electrode and a method of manufacturing an implantable optical electrode. The present application discloses a neuromodulation transfection system that combines multiple functions such as those disclosed herein in a form that includes highly adaptable positioning of the various components to optimize the system performance in a specific subject or application. Various features and advantages of the invention are set forth in the following claims.

What is claimed is:

1. An implantable neural device, comprising:
   a substrate having a substrate thickness extending from a first substrate face to a spaced apart second substrate face, wherein the first and second substrate faces extend from a proximal substrate portion to a distal substrate portion and wherein the substrate is planar and has a plurality of lateral edges;
   a plurality of electrodes supported by the substrate;
   a conductive trace extending from each electrode of the plurality of electrodes to a proximal trace end at the proximal substrate portion, wherein the proximal trace end is electrically connectable to an external instrumentation;
   a cavity extending partway through the substrate thickness, the cavity having a single opening formed in the first substrate face; and
   a delivery capsule received in the cavity, wherein the delivery capsule comprises a biologic or bioactive agent adapted to induce a therapeutic response from body tissue in which the neural device is implanted,
      wherein at least one electrode of the plurality of electrodes is located on the first substrate surface directly adjacent to the cavity such that the at least one electrode is co-localized with a portion of the body tissue that includes targeted cells that receive the biologic or bioactive agent; and
      wherein at least two electrodes of the plurality of electrodes are located closer to a lateral edge of the plurality of lateral edges of the substrate than the cavity.

2. The implantable neural device of claim 1, wherein the delivery capsule supports a permeable membrane covering the biologic or bioactive agent adjacent to the opening.

3. The implantable neural device of claim 1, wherein the cavity comprises a wall of the first substrate face projecting outwardly to the opening opposite the second substrate face.

4. The implantable neural device of claim 1, wherein the plurality of electrodes includes at least two of the group consisting of a neurosensing electrode, a neurostimulation electrode, and an electroporation electrode.

5. The implantable neural device of claim 1, wherein the plurality of electrodes includes at least two electrodes located between a light source supported by the substrate and the cavity containing the biologic or bioactive agent, and wherein the at least two electrodes include a neurosensing electrode and an electroporation electrode.

6. The implantable neural device of claim 1, wherein the plurality of electrodes includes at least one neurosensing electrode, at least one neurostimulation electrode, and at least one electroporation electrode.

7. The implantable neural device of claim 1, wherein the cavity is one of a plurality of cavities that receive a plurality of delivery capsules; wherein a plurality of light sources are supported by the substrate; and wherein the plurality of electrodes includes electrodes that are located closer to each of the plurality of lateral edges of the substrate than any of the plurality of cavities or the plurality of light sources.

8. The implantable neural device of claim 1, further comprising:
   an electrode located inside the cavity covered by the delivery capsule.

9. The implantable neural device of claim 1, wherein the distal substrate portion comprises a sharpened point.

10. The implantable neural device of claim 1, wherein the substrate is configured to wrap around tissue.

11. The implantable neural device of claim 1, wherein the cavity extends longitudinally along the substrate for a proximal cavity end closer to a proximal end of the proximal substrate portion than a distal cavity end.

12. The implantable neural device of claim 1, wherein there is more than one cavity in the substrate and wherein a different biologic or bioactive agent is received in a respective cavity extending partway through the substrate thickness from a different opening in the first substrate face.

13. The implantable neural device of claim 1, wherein the delivery capsule is of a matrix material containing the biologic or bioactive agent, and wherein the matrix material is selected from the group consisting of gelatin, hydrogels, polyepsilon-caprolactone, polylactic acid, polyglycolic acid, and poly(lactic-co-glycolic acid) (PGLA).

14. An implantable neural device, comprising:
   a substrate having a substrate thickness extending from a first substrate face to a spaced apart second substrate face, wherein the first and second substrate faces extend from a proximal substrate portion to a distal substrate portion, and wherein the substrate is planar and has a plurality of lateral edges;
   a plurality of electrodes supported by the substrate, wherein the plurality of electrodes includes at least one neurosensing electrode, at least one neurostimulation electrode, and at least one electroporation electrode;
   a conductive trace extending from each of the plurality of electrodes to a proximal trace end at the proximal substrate portion, wherein the proximal trace end is electrically connectable to an external instrumentation;
   a waveguide extending from a proximal waveguide portion to a distal waveguide portion, wherein the proximal waveguide portion is connectable to a light source;
   an aperture extending from the first substrate face through the substrate thickness to the second substrate face in the distal substrate portion, wherein the aperture allows transmission of light from the distal waveguide portion, wherein the distal waveguide portion is attached to the second substrate face adjacent to the aperture;
   a cavity extending partway through the substrate thickness from an opening in the first substrate face; and
   a delivery capsule received in the cavity, wherein the delivery capsule comprises a biologic or bioactive agent adapted to induce a light-sensitive or therapeutic response from body tissue in which the neural device is implanted,
   wherein at least two of the plurality of electrodes are located on the first substrate surface adjacent to the cavity and closer to a lateral edge of the plurality of lateral edges of the substrate than the cavity; and
   wherein at least two other electrodes of the plurality of electrodes are located closer to the lateral edge than the light source.

15. The implantable neural device of claim 14, wherein the delivery capsule supports a permeable membrane covering the biologic or bioactive agent adjacent to the opening.

16. The implantable neural device of claim 14, wherein the cavity comprises a wall of the first substrate face projecting outwardly to the opening opposite the second substrate face.

17. The implantable neural device of claim 14, wherein at least one other electrode of the plurality of electrodes is located between the cavity and the aperture.

18. The implantable neural device of claim 14, wherein the plurality of electrodes includes four first electrodes positioned around the light source and four second electrodes positioned around the cavity wherein two of the four first electrodes and two of the four second electrodes are located adjacent to each other between the light source and the cavity.

19. The implantable neural device of claim 14, wherein the delivery capsule comprises a polynucleotide which encodes for a light-sensitive ion channel.

20. The implantable neural device of claim 14, wherein the cavity is one of a plurality of cavities that receive a plurality of delivery capsules; wherein a plurality of light sources are supported by the substrate; and wherein the plurality of electrodes includes electrodes closer to each of the plurality of lateral edges than any of the plurality of cavities or the plurality of light sources.

21. The implantable neural device of claim 20, wherein the plurality of electrodes further comprises at least two electroporation electrodes on opposite sides of the aperture and adjacent to the cavity.

22. The implantable neural device of claim 14, wherein at least one of the plurality of electrodes is located inside the cavity covered by the delivery capsule.

23. The implantable neural device of claim 14, wherein the biologic or bioactive agent is a light-sensitive opsin.

24. An implantable neural device, comprising:
   a substrate having a substrate thickness extending from a first substrate face to a spaced apart second substrate face, wherein the first and second substrate faces extend from a proximal substrate portion to a distal substrate portion, and wherein the substrate is planar and has a plurality of lateral edges;
   a plurality of electrodes supported by the substrate, wherein the plurality of electrodes includes a neurosensing electrode, a neurostimulation electrode, and an electroporation electrode;
   a conductive trace extending from one of the plurality of electrodes to a proximal trace end at the proximal substrate portion, wherein the proximal trace end is electrically connectable to an external instrumentation;
   a waveguide extending from a proximal waveguide portion to a distal waveguide portion, wherein the proximal waveguide portion is connectable to a light source;
   an aperture extending from the first substrate face through the substrate thickness to the second substrate face in the distal substrate portion, wherein the distal waveguide portion is supported by the second substrate face adjacent to the aperture;
   a cavity at the distal substrate portion and extending partway through the substrate thickness from an opening in the first substrate face; and
   a delivery capsule in the cavity, wherein the delivery capsule comprises a biologic or bioactive agent adapted to induce a light-sensitive or therapeutic response from body tissue at a particular tissue location at which the implantable neural device is implanted,
   wherein the plurality of electrodes is substantially co-localized with the cavity and the aperture such that a same portion of the body tissue at the particular tissue location that includes targeted cells that receive the biologic or bioactive agent is also at least one of electropermeabilized by the electroporation electrode, sensed by the neurosensing electrode, or electrically stimulated by the neurostimulation electrode in a single procedure;
   wherein at least two of the plurality of electrodes are located on the first substrate surface adjacent to the cavity and closer to a lateral edge of the plurality of lateral edges of the substrate than the cavity; and
   wherein at least two other electrodes of the plurality of electrodes are located closer to the lateral edge than the light source.

25. The implantable neural device of claim 24, further comprising a permeable membrane covering the delivery capsule.

26. The implantable neural device of claim 24, wherein the cavity is one of a plurality of cavities that receive a plurality of delivery capsules; wherein a plurality of light sources are supported by the substrate; and wherein the plurality of electrodes includes electrodes closer to each of the plurality of lateral edges than any of the plurality of cavities or the plurality of light sources.

27. The implantable neural device of claim 24, wherein at least one of the plurality of electrodes is located inside the cavity.

28. The implantable neural device of claim 24, wherein there is more than one cavity in the substrate and wherein a different biologic or bioactive agent is received in a respective cavity.

29. The implantable neural device of claim 24, wherein the delivery capsule is of a resorbable or degradable matrix in which the biologic or bioactive agent is embedded.

30. The implantable neural device of claim 24, wherein the delivery capsule comprises a polynucleotide which encodes for a light-sensitive ion channel.

31. The implantable neural device of claim 24, wherein the cavity comprises a wall of the first substrate face projecting outwardly to the opening opposite the second substrate face.

32. The implantable neural device of claim 24, wherein the substrate is configured to wrap around tissue.

* * * * *